United States Patent [19] [11] 4,225,371
Taylor et al. [45] Sep. 30, 1980

[54] METHOD OF MAKING A CATHETER

[75] Inventors: Glenn N. Taylor, Cary; Bhupendra C. Patel, Elgin, both of Ill.

[73] Assignee: The Kendall Company, Boston, Mass.

[21] Appl. No.: 32,836

[22] Filed: Apr. 24, 1979

Related U.S. Application Data

[62] Division of Ser. No. 829,868, Sep. 1, 1977, Pat. No. 4,178,937.

[51] Int. Cl.³ .............................................. B32B 31/00
[52] U.S. Cl. .................................. 156/152; 29/455 R; 29/157 R; 156/252
[58] Field of Search .............. 29/157 R, 455 R, 469.5; 156/152, 250, 252; 128/349 B, 246

[56] References Cited

U.S. PATENT DOCUMENTS

| 1,490,454 | 4/1924 | Callan et al. | 156/152 X |
| 3,161,553 | 12/1964 | Visser | 156/252 X |
| 3,865,666 | 2/1975 | Shoney | 128/349 B X |
| 3,989,571 | 11/1976 | Harautuneian | 156/250 |
| 4,055,187 | 10/1977 | Patel et al. | 128/349 B |
| 4,106,509 | 8/1978 | McWhorter | 128/349 B |

Primary Examiner—Charlie T. Moon
Attorney, Agent, or Firm—Powell L. Sprunger

[57] ABSTRACT

A catheter comprising, an elongated shaft of elastic material having an annular sleeve overlying a surface of the shaft, with one end of the sleeve being of one-piece construction with the shaft, and with a circumferential portion of the sleeve spaced from the one sleeve end being bonded to the shaft to define a cavity between the sleeve and the shaft surface. The inflation lumen communicates with the cavity in order to inflate the balloon.

3 Claims, 6 Drawing Figures

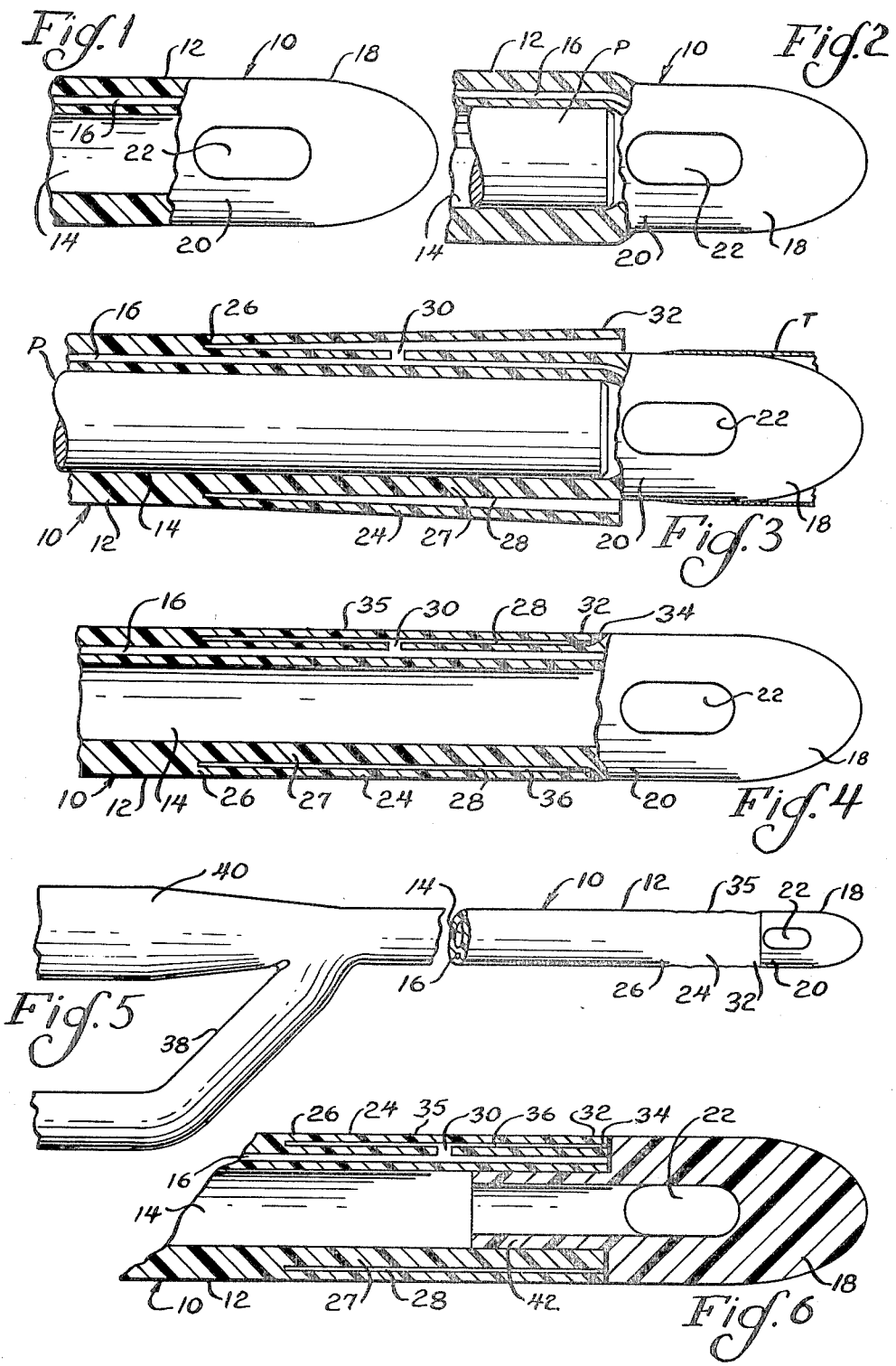

METHOD OF MAKING A CATHETER

This is a division of application Ser. No. 829,868 filed Sept. 1, 1977, now U.S. Pat. No. 4,178,937, issued Dec. 18, 1979.

BACKGROUND OF THE INVENTION

The present invention relates to catheters, and more particularly to balloon structures for such catheters.

In the past, a various assortment of catheters, such as Foley catheters and endotracheal tubes, have been proposed for use in patients. In the case of urinary catheters, a conventional Foley catheter is normally constructed having a shaft defining a drainage lumen extending from a drainage eye adjacent a distal end of the shaft and an inflation lumen in a wall of the shaft, and having an expansible balloon overlying a distal portion of the shaft and defining a cavity communicating with the inflation lumen. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

A great majority of Foley catheters have been made from latex rubber through dipping techniques known to the art. However, a number of problems have been encountered with conventional latex catheters, such as difficulties in manufacture and delamination of the catheter sidewalls causing blockage in the inflation lumen. Accordingly, there has been a desire to construct catheters from materials which display superior properties of performance. For example, it is preferred that the catheter shaft be made from a material which can be extruded in order to facilitate the manufacturing process and eliminate the delamination problems associated with dipped latex catheters. In addition, it is desirable to simplify construction of the balloon while achieving a satisfactory joinder between the balloon and shaft in order to reduce the cost of the catheter which is a disposable item.

SUMMARY OF THE INVENTION

A principal feature of the present invention is the provision of a catheter of simplified construction having an improved balloon.

The catheter of the present invention comprises, an elongated shaft of elastic material having a main lumen, an inflation lumen extending along the shaft, and an annular sleeve severed from an inner portion of the shaft. The sleeve is of one-piece construction with the shaft at one end of the sleeve with the other free end of the sleeve being bonded to the shaft to define a cavity intermediate the sleeve and the inner shaft portion. The catheter has an opening communicating between the inflation lumen and the cavity.

A feature of the present invention is that the sleeve defines an inflatable balloon which is part of the catheter shaft, and the sleeve is firmly joined to the shaft.

Thus, another feature of the invention is that the catheter eliminates the necessity of forming a separate sleeve and bonding the separate sleeve to the shaft.

Yet another feature of the invention is that the catheter may be made at a reduced cost.

Still another feature of the invention is the provision of methods for forming the catheter.

Further features will become more fully apparent in the following description of the embodiments of this invention and from the appended claims.

DESCRIPTION OF THE DRAWINGS

In the drawings:

FIGS. 1–4 are fragmentary elevational views, taken partly in section, illustrating steps in formation of a catheter according to the present invention;

FIG. 5 is a fragmentary elevational view of a catheter of the present invention; and FIG. 6 is a fragmentary sectional view of another embodiment of a catheter of the present invention.

DESCRIPTION OF THE PREFERRED EMBODIMENTS

Referring now to FIG. 1, there is shown a catheter generally designated 10 having an elongated shaft 12 of elastic material, such as an extruded material of silicone, polyvinyl chloride, or Kraton, a trademark of Shell Oil Company. Although the principals of the present invention will be discussed in connection with a Foley catheter, it will be understood that any suitable catheter may be constructed in the manner described, such as an endotracheal tube. As shown, the catheter shaft 12 has a main drainage lumen 14 extending through the shaft, and an inflation lumen 16 extending along the wall of the shaft. The catheter 10 has a tip 18 at a distal end 20 of the catheter, and a drainage eye 22 communicating with the main lumen 14 of the catheter shaft 12. In one form, as shown, the catheter tip 18 may be of one-piece construction with the shaft 12, and the tip 18 may be formed by heating the distal end of the catheter after extrusion of the catheter shaft.

With reference to FIG. 2, an elongated pin or cylinder P is inserted into the main lumen 14 of the catheter shaft 12 at a location adjacent the catheter tip 18. As shown, the pin P has a diameter larger than the diameter of the catheter lumen 14 in order to expand the catheter shaft. Next, with reference to FIG. 3, an annular cutting tool T is utilized to sever an annular outer wall section or sleeve 24 of the shaft 12 from an inner portion 27 of the shaft while leaving one end 26 of the sleeve 24 joined to the shaft 12. Thus, the one sleeve end 26 is of one-piece construction with the shaft 12, and the sleeve 24 overlies a surface 28 of the inner shaft portion 27. An opening 30 is then formed in the inner shaft portion 27 which communicates between the inflation lumen 16 and the shaft surface 28. Finally, with reference to FIG. 4, the other free sleeve end 32 is bonded to the catheter shaft in a circumferential region by a suitable means 34, such as by adhesive or heatsealing, and the pin is removed from the catheter lumen 14.

In this manner, an inflatable balloon 35 defined by the sleeve 24 is formed in a simplified manner through use of the catheter shaft itself. The sleeve 24 defines a cavity 36 intermediate the sleeve and the shaft surface 28, with the cavity 36 communicating with the inflation lumen 16 through the opening 30. With reference to FIG. 5, the balloon 35 may be inflated through valve means (not shown) on a sidearm 38 of the catheter and through the inflation lumen 16 at the time of use.

Thus, in accordance with the present invention, the inflatable balloon 35 is formed from the catheter shaft by severing the shaft, and by bonding a distal end of the severed sleeve to the shaft. In this manner, the catheter is formed of simplified structure in order to reduce its cost, and the balloon is securely joined to the catheter shaft. Although the balloon has been shown as being severed in a direction proximally along the shaft, it will be apparent that through use of a suitable pin, the balloon may be severed in a direction distally along the shaft, such that the free end of the sleeve is located proximal the integral sleeve end.

In use, the catheter shaft 12 is passed through the urethra of a patient until the balloon 35 is located in the bladder, and the balloon is inflated through the inflation lumen 16 in order to retain the catheter in place. Urine drains through the drainage eye 22 and main lumen 14 to a proximal end 40 of the catheter 10 which is connected to a drainage tube (not shown) and a drainage bag (not shown) for collection of the urine.

Another embodiment of the present invention is illustrated in FIG. 6, in which like reference numerals designate like parts. In this embodiment, the catheter 10 has a separate tip 18 having a tongue 42 received in the shaft lumen 14, with the tip 18 being bonded to a distal end of the shaft. The sleeve 24 is severed from the distal end of the catheter shaft prior to attachment of the tip, and the free sleeve end 32 is bonded to the catheter shaft to define an inflatable balloon 35, in a manner as previously described.

The foregoing detailed description is given for clearness of understanding only, and no unnecessary limitations should be understood therefrom, as modifications will be obvious to those skilled in the art.

We claim:

1. A method of making a catheter, comprising the steps of:
    forming an elongated shaft of elastic material having an inflation lumen extending along the shaft;
    severing an annular outer wall section of the shaft from an inner portion of the shaft while leaving one end of said section joined to the shaft;
    establishing communication between the inflation lumen and the surface of said inner shaft portion; and
    bonding a free end of said section to said shaft to define a cavity between said section and inner shaft portion.

2. The method of claim 1 including the step of expanding a portion of said shaft in the region of said section between said forming and severing steps.

3. The method of claim 1 wherein said severing step comprises the step of cutting the shaft in a direction proximally along the shaft.

* * * * *